US010633328B2

(12) United States Patent
Ebert et al.

(10) Patent No.: US 10,633,328 B2
(45) Date of Patent: Apr. 28, 2020

(54) POLYETHERAMINES BASED ON 1,3-DIALCOHOLS

(71) Applicant: BASF SE, Ludwigshafen (DE)

(72) Inventors: Sophia Ebert, Mannheim (DE); Björn Ludolph, Ludwigshafen (DE); Christof W. Wigbers, Mannheim (DE); Steffen Maas, Bubenheim (DE); Frank Huelskoetter, Bad Dürkheim (DE); Stefano Scialla, Rome (IT); Dieter Boeckh, Limburgerhof (DE); Kevin Christmas, Mason, OH (US); Amy Eichstadt Waun, West Chester, OH (US); Brian J. Loughnane, Sharonville, OH (US); Darren Rees, Newcastle upon Tyne (GB); Christian Eidamshaus, Mannheim (DE); Monika Charrak, Ludwigshafen (DE); Alexander Panchenko, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 834 days.

(21) Appl. No.: 14/780,603

(22) PCT Filed: Mar. 27, 2014

(86) PCT No.: PCT/EP2014/056118
§ 371 (c)(1),
(2) Date: Sep. 28, 2015

(87) PCT Pub. No.: WO2014/154783
PCT Pub. Date: Oct. 2, 2014

(65) Prior Publication Data
US 2016/0052867 A1 Feb. 25, 2016

(30) Foreign Application Priority Data
Mar. 28, 2013 (EP) .................................... 13161517

(51) Int. Cl.
*C07C 217/08* (2006.01)
*A61K 8/45* (2006.01)
(Continued)

(52) U.S. Cl.
CPC .............. *C07C 217/08* (2013.01); *A61K 8/45* (2013.01); *A61K 8/86* (2013.01); *A61Q 5/02* (2013.01);
(Continued)

(58) Field of Classification Search
None
See application file for complete search history.

(56) References Cited

U.S. PATENT DOCUMENTS 3,862,227 A * 1/1975 Haug .................. C08G 59/504
558/389
4,820,436 A 4/1989 Andree et al.
(Continued)

FOREIGN PATENT DOCUMENTS

CA 00972096 A 7/1975
DE 011363 A 3/1956
(Continued)

OTHER PUBLICATIONS

International Search Report for PCT/EP2014/056118 dated May 27, 2014.
Skarzewski, J., et al., "Lipophilic Complexones, Part 3[1], Synthesis of Polyamines Derived from 2-Alkyl-1,3-propanediols and 2,2-Bis(hydroxymethyl)alkanols", Monatshefte für Chemie 114, (1983), pp. 1071-1077.
Chekulayeva, I., et. al., "Synthesis of New Heterochain Polyamines by Reaction of Diamines With Diacetylene", Polymer Science U.S.S.R., 1970, vol. 12, No. 5, pp. 1339-1345.
(Continued)

*Primary Examiner* — Patrick Lewis
(74) *Attorney, Agent, or Firm* — Drinker Biddle & Reath LLP

(57) ABSTRACT

This invention relates to polyetheramines based on 1,3-dialcohols, in particular to an etheramine mixture comprising at least 90% by weight, based on the total weight of the etheramine mixture, of anamine of Formula (I) and/or (II), wherein $R_1$-$R_{12}$ are independently selected from H, alkyl, cycloalkyl, aryl, alkylaryl, or arylalkyl, wherein at least one of $R_1$-$R_6$ and at least one of $R_7$-$R_{12}$ is different from H, wherein $A_1$-$A_9$ are independently selected from linear or branched alkylenes having 2 to 18 carbon atoms, preferably 2-10 carbon atoms, most preferably 2-5 carbon atoms, wherein $Z_1$-$Z_4$ are independently selected from OH or $NH_2$, wherein at least one of $Z_1$-$Z_2$ and at least one of $Z_3$-$Z_4$ is $NH_2$, and wherein the sum of x+y is in the range of from 2 to 200, wherein x≥1 and y≥1; and $x_1$+$y_1$ is in the range of from 2 to 200, preferably 2-20, most preferably 2-10, wherein $x_1$≥1 and $y_1$≥1.

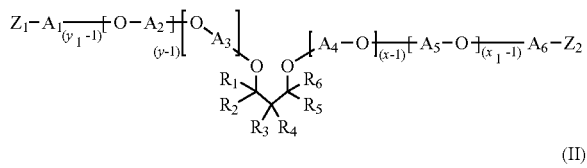

(I)

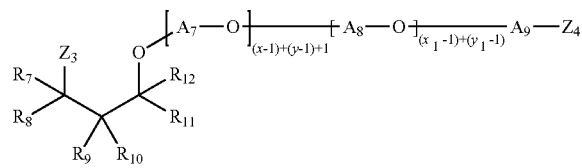

(II)

24 Claims, No Drawings

(51) Int. Cl.
*A61Q 5/02* (2006.01)
*A61K 8/86* (2006.01)
*A61Q 19/10* (2006.01)
*C11D 1/44* (2006.01)
*C07C 41/03* (2006.01)
*C07C 213/02* (2006.01)
*C08G 59/50* (2006.01)
*C11D 3/37* (2006.01)
*C07C 211/13* (2006.01)
*C07C 211/01* (2006.01)
*C07C 211/09* (2006.01)
*C07C 211/02* (2006.01)

(52) U.S. Cl.
CPC .............. *A61Q 19/10* (2013.01); *C07C 41/03* (2013.01); *C07C 213/02* (2013.01); *C08G 59/504* (2013.01); *C11D 1/44* (2013.01); *C11D 3/3707* (2013.01); *C07C 211/01* (2013.01); *C07C 211/02* (2013.01); *C07C 211/09* (2013.01); *C07C 211/13* (2013.01)

(56) References Cited

U.S. PATENT DOCUMENTS

| | | |
|---|---|---|
| 5,530,127 A | 6/1996 | Reif et al. |
| 8,318,982 B2 | 11/2012 | Kubanek et al. |
| 8,487,135 B2 | 7/2013 | Kubanek et al. |
| 8,519,084 B2 | 8/2013 | Mijolovic et al. |
| 8,530,570 B2 | 9/2013 | Mijolovic et al. |
| 2011/0040030 A1 | 2/2011 | Mijolovic et al. |
| 2011/0144259 A1 | 6/2011 | Mijolovic et al. |
| 2011/0178239 A1 | 7/2011 | Mijolovic et al. |
| 2013/0123160 A1 | 5/2013 | Dobrawa et al. |
| 2013/0123372 A1 | 5/2013 | Dobrawa et al. |
| 2013/0137901 A1 | 5/2013 | Strautmann et al. |
| 2013/0253089 A1 | 9/2013 | El-Toufaili et al. |
| 2013/0303725 A1 | 11/2013 | Dobrawa et al. |
| 2013/0310300 A1 | 11/2013 | Leyrer et al. |
| 2014/0024780 A1 | 1/2014 | Benlahmar et al. |
| 2014/0288265 A1 | 9/2014 | Ebert et al. |
| 2015/0210952 A1 | 7/2015 | Desantis et al. |

FOREIGN PATENT DOCUMENTS

| | | |
|---|---|---|
| EP | 696572 A1 | 2/1996 |
| GB | 581994 A | 10/1946 |
| GB | 1226122 A | 3/1971 |
| JP | S6445684 A | 2/1989 |
| JP | 200515617 A | 1/2005 |
| KR | 20120078540 A | 7/2012 |
| WO | WO-86/007603 A1 | 12/1986 |
| WO | WO-90/003423 A1 | 4/1990 |
| WO | WO-0176729 A2 | 10/2001 |
| WO | WO-2009065738 A2 | 5/2009 |
| WO | WO-09138387 A1 | 11/2009 |
| WO | WO-09153193 A1 | 12/2009 |
| WO | WO-10010075 A1 | 1/2010 |
| WO | WO-10026030 A1 | 3/2010 |
| WO | WO-10026066 A1 | 3/2010 |
| WO | WO-2010062158 A2 | 6/2010 |
| WO | WO-2011/067199 A1 | 6/2011 |
| WO | WO-2011/067200 A1 | 6/2011 |
| WO | WO-2011087793 A1 | 7/2011 |
| WO | WO-2013/072289 A1 | 5/2013 |
| WO | WO-2014012375 A1 | 1/2014 |
| WO | WO-2014154783 A1 | 10/2014 |

OTHER PUBLICATIONS

English Translation of Japanese Office Action for Japanese Application No. 504667/2016, dated Feb. 6, 2018.
Registry [Online] STN Tokyo, 2010, CAS registry No. 1220986-59-3, p. 8.

* cited by examiner

POLYETHERAMINES BASED ON 1,3-DIALCOHOLS

CROSS-REFERENCE TO RELATED APPLICATIONS

This application is a national stage application (under 35 U.S.C. § 371) of PCT/EP2014/056118, filed Mar. 27, 2014, which claims benefit of European Application No. 13161517.1, filed Mar. 28, 2013, both of which are incorporated herein by reference in their entirety.

This invention relates to polyetheramines based on 1,3-dialcohols, in particular to polyetheramine mixtures obtainable by the alkoxylation and amination of 1,3-dialcohols.

Due to the increasing popularity of easy-care fabrics made of synthetic fibers as well as the ever increasing energy costs and growing ecological concerns of detergent users, the once popular hot water wash has now taken a back seat to washing fabrics in cold water. Many commercially available laundry detergents are even advertised as being suitable for washing fabrics at 40° C. or 30° C. or even at room temperature. To achieve satisfactory washing result at such low temperatures, results comparable to those obtained with hot water washes, the demands on low-temperature detergents are especially high.

It is known to include certain additives in detergent compositions to enhance the detergent power of conventional surfactants so as to improve the removal of grease stains at temperatures of 60° C. and below.

WO 86/07603 discloses that detergent composition comprising an aliphatic amine compound, in addition to at least one synthetic anionic and/or nonionic surfactant, are known and have led to improved cleaning results even at low wash temperatures. These compounds are said to contribute to the improvement of the washing performance of the detergent at lower temperatures.

Also, the use of linear, alkyl-modified (secondary) alkoxypropylamines in laundry detergents to improve cleaning at low temperatures is known (WO90/03423). These known laundry detergents, however, are unable to achieve satisfactory cleaning when laundry is washed at cold temperatures.

Furthermore, the use of linear, primary polyoxyalkyleneamines (e.g., Jeffamine® D-230) to stabilize fragrances in laundry detergents and provide longer lasting scent is also known (WO2009/065738). Also, the use of high-molecular-weight (molecular weight of at least about 1000), branched, trifunctional, primary amines (e.g., Jeffamine® T-5000 polyetheramine) to suppress suds in liquid detergents is known (WO01/76729).

Additionally, WO 2011/087793 reads on etheramine mixtures comprising at least 10 wt % of an alkoxylated monoether amine based on polyhydric alcohols containing 2 to 4 hydroxyl groups as the starting compound. A process for the manufacture of these etheramine mixtures is also disclosed. These products find an application as a curing agent or as a raw material in the synthesis of polymers.

There is a continuous need for cleaning compositions that remove grease stains from fabrics and other soiled materials, as grease stains are challenging stains to remove. Conventional cleaning compositions directed to grease removal frequently utilize various amine compounds which tend to show strong negative impacts on whiteness. As a consequence there is still a continual need for improved amine compositions which provide improved grease removal from fabrics and other soiled materials and at the same time do not negatively impact the clay cleaning.

It was an object of the present invention to provide compounds which would improve the washing performance of detergents at low temperatures, i.e. at temperatures as low as 30° C. or even lower.

This goal was achieved with an etheramine mixture comprising at least 90% by weight, based on the total weight of the etheramine mixture, of an amine of Formula (I) and/or (II),

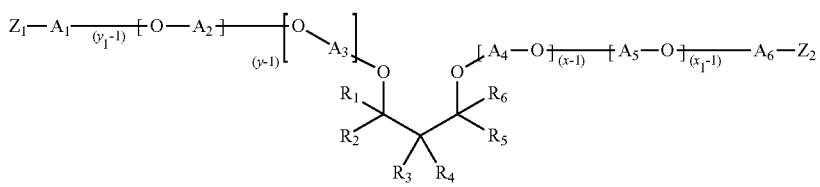

Formula (I)

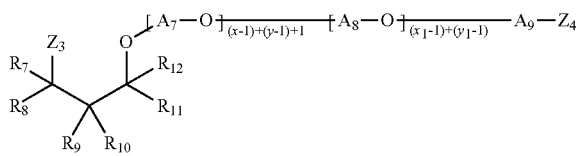

Formula (II)

wherein $R_1$-$R_{12}$ are independently selected from H, alkyl, cycloalkyl, aryl, alkylaryl, or arylalkyl, wherein at least one of $R_1$-$R_6$ and at least one of $R_7$-$R_{12}$ is different from H, wherein $A_1$-$A_9$ are independently selected from linear or branched alkylenes having 2 to 18 carbon atoms, preferably 2-10 carbon atoms, most preferably 2-5 carbon atoms, wherein $Z_1$-$Z_4$ are independently selected from OH or $NH_2$, wherein at least one of $Z_1$-$Z_2$ and at least one of $Z_3$-$Z_4$ is $NH_2$, and wherein the sum of x+y is in the range of about 2 to about 200, wherein x≥1 and y≥1; and $x_1$+$y_1$ is in the range of about 2 to about 200, preferably 2-20, most preferably 2-10, wherein $x_1$≥1 and $y_1$≥1.

Preferably, the sum of x and y is in the range of 2 to 20, more preferably in the range of 2 to 10, even more preferably in the range of 3 to 8 and even more preferably in the range of 4 to 6.

Preferably, the sum of $x_1$ and $y_1$ is in the range of 2 to 20, more preferably in the range of 2 to 10, even more preferably in the range of 3 to 8 and even more preferably in the range of 2 to 4.

In a preferred embodiment, the etheramine mixture comprises at least 95% by weight, based on the total weight of the etheramine mixture, of the amine of Formula (I) and/or (II).

In another preferred embodiment, $A_1$-$A_9$ are independently selected from the group consisting of ethylene, propylene, or butylene, preferably each of $A_1$-$A_9$ is propylene.

In Formula (I) or (II), $R_1$, $R_2$, $R_5$, $R_6$, $R_7$, $R_8$, $R_{11}$, and $R_{12}$ are H and $R_3$, $R_4$, $R_9$, and $R_{10}$ are independently selected from C1-16 alkyl or aryl.

Preferably, in Formula (I) or (II), $R_1$, $R_2$, $R_5$, $R_6$, $R_7$, $R_8$, $R_{11}$, and $R_{12}$ are H and $R_3$, $R_4$, $R_9$, and $R_{10}$ are independently selected from a butyl group, an ethyl group, a methyl group, a propyl group, or a phenyl group.

Even more preferably, in Formula (I) or (II), R3 and R9 are each an ethyl group, $R_1$, $R_2$, $R_5$, $R_6$, $R_7$, $R_8$, $R_{11}$, and $R_{12}$ are each H, R4 and R10 are each a butyl group.

The polyetheramine of Formula (I) or Formula (II) has a weight average molecular weight of about 290 to about 1000 grams/mole, preferably, of about 300 to about 700 grams/mole, even more preferably of about 300 to about 450 grams/mole.

The etheramine mixture comprising at least 90% by weight, based on the total weight of the etheramine mixture, of an etheramin of Formula (I) and/or (II) is obtainable by a process comprising the following steps:
a) the reaction of 1,3-diols of Formula (III) with $C_2$-$C_{18}$ alkylene oxides, wherein the molar ratio of 1,3-diol to $C_2$-$C_{18}$ alkylene oxides is in the range of 1:2 to 1:10,

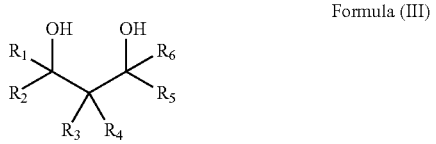

Formula (III)

with $R_1$-$R_6$ are independently of one another H, alkyl, cycloalkyl, aryl, alkylaryl, arylalkyl and at least one group selected from $R_1$-$R_6$ is different from H,
b) the amination of the alkoxylated 1,3-diols with ammonia.

In a preferred embodiment, this etheramine mixture comprising at least 95% by weight, based on the total weight of the etheramine mixture, of the obtained etheramine.

In a preferred embodiment the molar ratio of 1,3-diol to $C_2$-$C_{18}$ alkylene oxides is in the range of 1:3 to 1:8, even more preferably in the range of 1:4 to 1:6.

Preferably the $C_2$-$C_{18}$ alkylene oxides are selected from the group consisting of ethylene oxide, propylene oxide, butylene oxide or a mixture thereof, even more preferably $C_2$-$C_{18}$ alkylene oxide is propylene oxide.

Preferably in the 1,3-diol of Formula (III) $R_1$, $R_2$, $R_5$, $R_6$ are H and $R_3$, $R_4$ are C1-16 alkyl or aryl.

The 1,3-diol of Formula (III) is preferably selected from the group consisting of 2-butyl-2-ethyl-1,3-propanediol, 2-methyl-2-propyl-1,3-propanediol, 2-methyl-2-phenyl-1,3-propanediol, 2,2-dimethyl-1,3-propandiol, 2-ethyl-1,3-hexandiol.

Step a): Alkoxylation

Substituted 1,3 diols (Formula III) are synthesized according WO10026030, WO10026066, WO09138387, WO09153193, WO10010075.

Suitable 1,3-diols (Formula III) are for example: 2,2-dimethyl-1,3-propane diol, 2-butyl-2-ethyl-1,3-propane diol, 2-pentyl-2-propyl-1,3-propane diol, 2-(2-methyl)butyl-2-propyl-1,3-propane diol, 2,2,4-trimethyl-1,3-propane diol, 2,2-diethyl-1,3-propane diol, 2-methyl-2-propyl-1,3-propane diol, 2-ethyl-1,3-hexane diol, 2-phenyl-2-methyl-1,3-propane diol, 2-methyl-1,3-propane diol, 2-ethyl-2-methyl-1,3 propane diol, 2,2-dibutyl-1,3-propane diol, 2,2-di(2-methylpropyl)-1,3-propane diol, 2-isopropyl-2-methyl-1,3-propane diol, etc.

Preferred 1,3-diols are 2-butyl-2-ethyl-1,3-propanediol, 2-methyl-2-propyl-1,3-propanediol, 2-methyl-2-phenyl-1,3-propanediol.

Alkoxylated 1,3-diols are obtained by reaction of 1,3-diols (Formula III) with alkylene oxides and can be affected according to general alkoxylation procedures known in the art.

The alkoxylated 1,3-diols may be prepared in a known manner by reaction of 1,3-diols with alkylene oxides. Suitable alkylene oxides are $C_2$-$C_{18}$ alkylene oxides like ethylene oxide, propylene oxide, butylene oxide, pentene oxide, hexene oxide, decene oxide, dodecene oxide etc. Preferred $C_2$-$C_{18}$ alkylene oxides are ethylene oxide, propylene oxide, butylene oxide or a mixture thereof.

The 1,3-diols are reacted with one single alkylene oxide or combinations of two or more different alkylene oxides. Using two or more different alkylene oxides, the resulting polymer can be obtained as a block-wise structure or a random structure.

The molar ratio of molar ratio of 1,3-diol to $C_2$-$C_{18}$ alkylene oxides at which the alkoxylation reaction is carried out lies in the range of 1:2 to 1:10, preferably in the range of 1:3 to 1:8, even more preferably in the range of 1:4 to 1:6.

This reaction is undertaken generally in the presence of a catalyst in an aqueous solution at a reaction temperature from about 70 to about 200° C. and preferably from about 80 to about 160° C. This reaction may be affected at a pressure of up to about 10 bar, and in particular up to about 8 bar.

Examples of suitable catalysts are basic catalysts such as alkali metal and alkaline earth metal hydroxides such as sodium hydroxide, potassium hydroxide and calcium hydroxide, alkali metal alkoxides, in particular sodium and potassium $C_1$-$C_4$-alkoxides, such as sodium methoxide, sodium ethoxide and potassium tert-butoxide, alkali metal and alkaline earth metal hydrides such as sodium hydride and calcium hydride, and alkali metal carbonates such as sodium carbonate and potassium carbonate. Preference is given to alkali metal hydroxides, particular preference being given to potassium hydroxide and sodium hydroxide. Typical use amounts for the base are from 0.05 to 10% by weight, in particular from 0.1 to 2% by weight, based on the total amount of polyalkyleneimine and alkylene oxide.

Alkoxylation with x+y $C_2$-$C_{18}$ alkylene oxides leads to structures as drawn in Formula IV and/or Formula V Formula (IV)

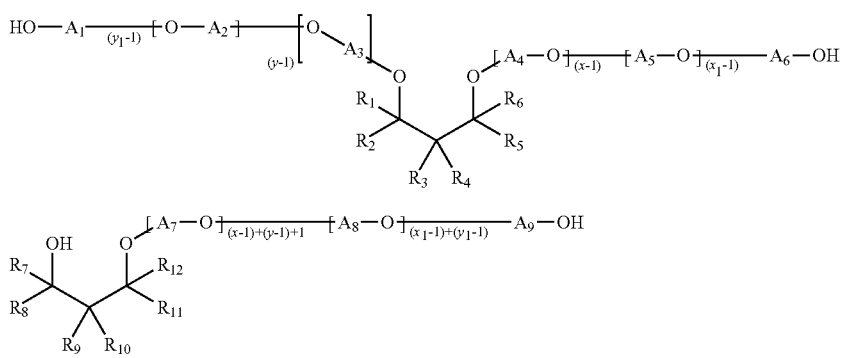

Formula (V)

wherein $R_1$-$R_{12}$ are independently selected from H, alkyl, cycloalkyl, aryl, alkylaryl, or arylalkyl, wherein at least one of $R_1$-$R_6$ and at least one of $R_7$-$R_{12}$ is different from H, wherein $A_1$-$A_9$ are independently selected from linear or branched alkylenes having 2 to 18 carbon atoms, preferably 2-10 carbon atoms, most preferably 2-5 carbon atoms, and wherein the sum of x+y is in the range of about 2 to about 200, wherein x≥1 and y≥1; and $x_1$+$y_1$ is in the range of about 2 to about 200, preferably 2-20, most preferably 2-10, wherein $x_1$≥1 and $y_1$≥1.

Step b): Amination

Amination of the alkoxylated 1,3-diols leads to new structures with Formula I and/or (II):

Formula (I)

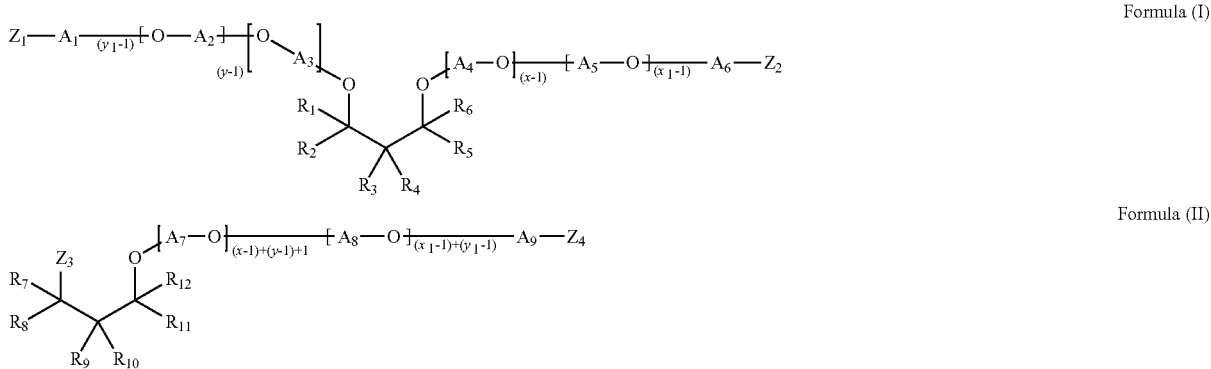

Formula (II)

wherein $R_1$-$R_{12}$ are independently selected from H, alkyl, cycloalkyl, aryl, alkylaryl, or arylalkyl, wherein at least one of $R_1$-$R_6$ and at least one of $R_7$-$R_{12}$ is different from H, wherein $A_1$-$A_9$ are independently selected from linear or branched alkylenes having 2 to 18 carbon atoms, preferably 2-10 carbon atoms, most preferably 2-5 carbon atoms, wherein $Z_1$-$Z_4$ are independently selected from OH or $NH_2$, wherein at least one of $Z_1$-$Z_2$ and at least one of $Z_3$-$Z_4$ is $NH_2$, and wherein the sum of x+y is in the range of about 2 to about 200, wherein x≥1 and y≥1; and $x_1$+$y_1$ is in the range of about 2 to about 200, preferably 2-20, most preferably 2-10, wherein $x_1$≥1 and $y_1$≥1.

Polyetheramines according to Formula (I) and/or (II) are obtained by reductive amination of the alkoxylated 1,3-diol mixture (Formula IV and V) with ammonia in presence of hydrogen and a catalyst containing nickel. Suitable catalysts are described in WO 2011/067199 A1 and in WO2011/067200 A1, and in EP0696572 B1. Preferred catalysts are supported copper-, nickel- and cobalt-containing catalysts, wherein the catalytically active material of the catalysts, before the reduction thereof with hydrogen, comprises oxygen compounds of aluminium, of copper, of nickel and of cobalt, and in the range from 0.2 to 5.0% by weight of oxygen compounds of tin, calculated as SnO. Other preferred catalysts are supported copper-, nickel- and cobalt-containing catalysts, wherein the catalytically active material of the catalysts, before the reduction thereof with hydrogen, comprises oxygen compounds of aluminium, of copper, of nickel, of cobalt and of tin, and in the range from 0.2 to 5.0% by weight of oxygen compounds of yttrium, of lanthanum, of cerium and/or of hafnium, each calculated as $Y_2O_3$, $La_2O_3$, $Ce_2O_3$ and $Hf_2O_3$ respectively. Another preferred catalyst is a zirconium, copper, nickel catalyst, wherein the catalytically active composition comprises from 20 to 85% by weight of oxygen-containing zirconium compounds, calculated as $ZrO2$, from 1 to 30% by weight of oxygen-containing compounds of copper, calculated as CuO, from 30 to 70% by weight of oxygen-containing compounds of nickel, calculated as NiO, from 0.1 to 5% by weight of oxygen-containing compounds of aluminium and/or manganese, calculated as $Al2O3$ and $MnO2$ respectively.

For the reductive amination step as well supported as non-supported catalyst can be used. The supported catalyst e.g. is obtained by deposition of the metallic components of the catalyst compositions onto support materials known to those skilled in the art, using techniques which are well-known in the art including without limitation, known forms of alumina, silica, charcoal, carbon, graphite, clays, mordenites; and molecular sieves, to provide supported catalysts as well. When the catalyst is supported, the support particles of the catalyst may have any geometric shape, for example the shape of spheres, tablets or cylinders in a regular or irregular version.

The process can be carried out in a continuous or discontinuous mode, e.g. in an autoclave, tube reactor or fixed-bed reactor. The reactor design is also not narrowly critical. The feed thereto may be upflowing or downflowing, and design features in the reactor which optimize plug flow in the reactor may be employed.

Byproducts which contain secondary or tertiary amino functions may be formed under amination reaction conditions. Secondary amines are e.g. obtained from a reaction of a fully or partially aminated diol with another fully and/or partially aminated diol. Tertiary amines are formed e.g. via a reaction of a secondary amine with another fully or partially aminated diol.

The degree of amination is between 50 to 100%, preferably from 60 to 100% and more preferably from 70-100% and even more preferably from 90 to 100%.

The degree of amination is calculated from the total amine value (AZ) divided by sum of the total acetylables value (AC) and tertiary amine value (tert. AZ) multiplicated by 100: (Total AZ: (AC+tert. AZ)×100).

The total amine value (AZ) is determined according to DIN 16945.

The total acetylables value (AC) is determined according to DIN 53240.

The secondary and tertiary amine are determined according to ASTM D2074-07.

The hydroxyl value is calculated from (total acetylables value+tertiary amine value)−total amine value.

In another preferred embodiment, the etheramines of the invention can also be further reacted with an acid. The acid may be selected from the group consisting of citric acid, lactic acid, sulfuric acid, methanesulfonic acid, hydrogen chloride, phosphoric acid, formic acid, acetic acid, propionic acid, valeric acid, oxalic acid, succinic acid, adipic acid, sebacic acid, glutaric acid, glucaric acid, tartaric acid, malic acid, benzoic acid, salicylic acid, phthalic acid, oleic acid, stearic acid and mixtures thereof. In an alternative embodiment, the etheramines of the invention may, in protonated form, have a surfactant as a counter ion, as obtained from e.g. linear alkyl benzene sulphonic acid.

Tertiary dialkyl-substituted polyether amines can be prepared from the respective primary polyether amines by reductive amination. Typical procedures involve the use of formaldehyde or other alkylaldehydes like ethanal, 1-propanal or 1-butanal in the presence of a hydrogen donor such as formic acid or the in the presence of hydrogen gas and a transition metal containing catalyst.

Alternatively, dialky-substituted tertiary polyether amines can be obtained by reacting a polyether alcohol with a dialkylamine like e.g. dimethylamine in the presence of a suitable transition metal catalyst, preferably in the additional presence of hydrogen and under continuous removal of the reaction water.

Applications:

The inventive etheramine mixtures may be used in personal care, especially in shampoo and body wash formulations.

They may also be used as curing agent for epoxy resins or as a reactant in the production of polymers but also in polyurethanes, polyureas, epoxy resins, polyamides.

The inventive polyetheramines have proved to be effective for removal of stains, particularly grease, from soiled material. Besides, cleaning compositions with inventive polyetheramines also do not have the cleaning negatives seen with conventional, amine cleaning compositions for hydrophilic bleachable stains, such as coffee, tea, wine, or particulates. Additionally, for stain removal from white fabric, cleaning compositions with inventive polyetheramines do not cause the whiteness negatives that commercially available, amine cleaning compositions cause.

A further advantage of cleaning compositions comprising the inventive polyetheramines is their ability to remove grease stains in cold water cleaning solutions, via pretreatment of the grease stain outside the washing machine, followed by cold water washing. Without being limited by theory, cold water solutions have the effect of causing greases to harden or solidify, making greases more resistant to removal, especially from fabric. Cleaning compositions with etheramine mixtures according to Formula (I) and/or (II) however, are surprisingly effective when used in pretreatment followed by cold water cleaning.

As used herein the phrase "cleaning composition" includes compositions and formulations designed for cleaning soiled material. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, liquid hand dishwashing composition, detergent contained on or in a porous substrate or nonwoven sheet, automatic dish-washing agent, hard surface cleaner, and other suitable forms that may be apparent to one skilled in the art in view of the teachings herein. Such compositions may be used as a pre-laundering treatment, a post-laundering treatment, may be added during the rinse or wash cycle of the laundering operation, or used in homecare cleaning applications. The cleaning compositions may have a form selected from liquid, powder, single-phase or multi-phase unit dose, pouch, tablet, gel, paste, bar, or flake.

The cleaning compositions described herein may include from about 0.1% to about 10%, in some examples, from about 0.2% to about 5%, and in other examples, from about 0.5% to about 3%, by weight the composition, of an amine-terminated polyalkylene glycol of Formula I and/or II.

The inventive etheramine mixtures are effective for removal of stains, particularly grease, from soiled material. Cleaning compositions containing the amine-terminated polyalkylene glycols of the invention also do not exhibit the cleaning negatives seen with conventional amine-containing cleaning compositions on hydrophilic bleachable stains, such as coffee, tea, wine, or particulates. Additionally, unlike conventional amine-containing cleaning compositions, the amine-terminated polyalkylene glycols of the invention do not contribute to whiteness negatives on white fabrics.

A further advantage of cleaning compositions containing the inventive etheramine mixture is their ability to remove grease stains in cold water, for example, via pretreatment of a grease stain followed by cold water washing. Without being limited by theory, it is believed that cold water washing solutions have the effect of hardening or solidifying grease, making the grease more resistant to removal, especially on fabric. Cleaning compositions containing the amine-terminated polyalkylene glycols of the invention are surprisingly effective when used as part of a pretreatment regimen followed by cold water washing.

Surfactant System

The cleaning compositions comprise a surfactant system in an amount sufficient to provide desired cleaning properties. In some embodiments, the cleaning composition comprises, by weight of the composition, from about 1% to about 70% of a surfactant system. In other embodiments, the liquid cleaning composition comprises, by weight of the composition, from about 2% to about 60% of the surfactant system. In further embodiments, the cleaning composition comprises, by weight of the composition, from about 5% to about 30% of the surfactant system. The surfactant system may comprise a detersive surfactant selected from anionic surfactants, nonionic surfactants, cationic surfactants, zwitterionic surfactants, amphoteric surfactants, ampholytic surfactants, and mixtures thereof. Those of ordinary skill in the art will understand that a detersive surfactant encompasses any surfactant or mixture of surfactants that provide cleaning, stain removing, or laundering benefit to soiled material.

Adjunct Cleaning Additives

The cleaning compositions of the invention may also contain adjunct cleaning additives. Suitable adjunct cleaning additives include builders, structurants or thickeners, clay soil removal/anti-redeposition agents, polymeric soil release agents, polymeric dispersing agents, polymeric grease cleaning agents, enzymes, enzyme stabilizing systems, bleaching compounds, bleaching agents, bleach activators, bleach catalysts, brighteners, dyes, hueing agents, dye transfer inhibiting agents, chelating agents, suds supressors, softeners, and perfumes.

Methods of Use

The present invention includes methods for cleaning soiled material. As will be appreciated by one skilled in the art, the cleaning compositions of the present invention are suited for use in laundry pretreatment applications, laundry cleaning applications, and home care applications.

Such methods include, but are not limited to, the steps of contacting cleaning compositions in neat form or diluted in wash liquor, with at least a portion of a soiled material and then optionally rinsing the soiled material. The soiled material may be subjected to a washing step prior to the optional rinsing step.

For use in laundry pretreatment applications, the method may include contacting the cleaning compositions described herein with soiled fabric. Following pretreatment, the soiled fabric may be laundered in a washing machine or otherwise rinsed.

Machine laundry methods may comprise treating soiled laundry with an aqueous wash solution in a washing machine having dissolved or dispensed therein an effective amount of a machine laundry cleaning composition in accord with the invention. An "effective amount" of the cleaning composition means from about 20 g to about 300 g of product dissolved or dispersed in a wash solution of volume from about 5 L to about 65 L. The water temperatures may range from about 5° C. to about 100° C. The water to soiled material (e.g., fabric) ratio may be from about 1:1 to about 20:1. In the context of a fabric laundry composition, usage levels may also vary depending not only on the type and severity of the soils and stains, but also on the wash water temperature, the volume of wash water, and the type of washing machine (e.g., top-loading, front-loading, top-loading, vertical-axis Japanese-type automatic washing machine).

The cleaning compositions herein may be used for laundering of fabrics at reduced wash temperatures. These methods of laundering fabric comprise the steps of delivering a laundry cleaning composition to water to form a wash liquor and adding a laundering fabric to said wash liquor, wherein the wash liquor has a temperature of above 0° C. to about 20° C., or to about 15° C., or to about 10° C. The fabric may be contacted to the water prior to, or after, or simultaneous with, contacting the laundry cleaning composition with water.

Another method includes contacting a nonwoven substrate impregnated with an embodiment of the cleaning composition with soiled material. As used herein, "nonwoven substrate" can comprise any conventionally fashioned nonwoven sheet or web having suitable basis weight, caliper (thickness), absorbency, and strength characteristics. Non-limiting examples of suitable commercially available nonwoven substrates include those marketed under the tradenames SON-TARA® by DuPont and POLYWEB® by James River Corp.

Hand washing methods, and combined handwashing with semiautomatic washing machines, are also included.

Machine Dishwashing Methods

Methods for machine-dishwashing or hand dishwashing soiled dishes, tableware, silverware, or other kitchenware, are included. One method for machine dishwashing comprises treating soiled dishes, tableware, silverware, or other kitchenware with an aqueous liquid having dissolved or dispensed therein an effective amount of a machine dishwashing composition in accord with the invention. By an effective amount of the machine dishwashing composition it is meant from about 8 g to about 60 g of product dissolved or dispersed in a wash solution of volume from about 3 L to about 10 L.

One method for hand dishwashing comprises dissolution of the cleaning composition into a receptacle containing water, followed by contacting soiled dishes, tableware, silverware, or other kitchenware with the dishwashing liquor, then hand scrubbing, wiping, or rinsing the soiled dishes, tableware, silverware, or other kitchenware. Another method for hand dishwashing comprises direct application of the cleaning composition onto soiled dishes, tableware, silverware, or other kitchenware, then hand scrubbing, wiping, or rinsing the soiled dishes, tableware, silverware, or other kitchenware. In some examples, an effective amount of cleaning composition for hand dishwashing is from about 0.5 ml. to about 20 ml. diluted in water.

Packaging for the Compositions

The cleaning compositions described herein can be packaged in any suitable container including those constructed from paper, cardboard, plastic materials, and any suitable laminates. An optional packaging type is described in European Application No. 94921505.7.

Multi-Compartment Pouch Additive

The cleaning compositions described herein may also be packaged as a multi-compartment cleaning composition.

SYNTHESIS EXAMPLES

Example 1

1 mol 2-Butyl-2-ethyl-1,3-propane diol+4 mol propylene oxide, aminated a) 1 mol 2-Butyl-2-ethyl-1,3-propane diol+4 mol propylene oxide In a 2 l autoclave 322.6 g 2-Butyl-2-ethyl-1,3-propane diol and 7.9 g KOH (50% in water) were mixed and stirred under vacuum (<10 mbar) at 120° C. for 2 h. The autoclave was purged with nitrogen and heated to 140° C. 467.8 g propylene oxide was added in portions within 6 h. To complete the reaction, the mixture was allowed to post-react for additional 5 h at 140° C. The reaction mixture was stripped with nitrogen and volatile compounds were removed in vacuo at 80° C. The catalyst potassium hydroxide was removed by adding 2.3 g synthetic magnesium silicate (Macrosorb MP5plus, Ineos Silicas Ltd.), stirring at 100° C. for 2 h and filtration. A yellowish oil was obtained (772.0 g, hydroxy value: 248.5 mgKOH/g).

b) 1 mol 2-Butyl-2-ethyl-1,3-propane diol+4 mol propylene oxide, aminated

In a 9 l autoclave 600 g of the resulting diol mixture from example 1-a, 1250 g THF and 1500 g ammonia were mixed in presence of 200 ml of a solid catalyst as described in EP0696572B1. The catalyst containing nickel, cobalt, copper, molybdenum and zirconium was in the form of 3×3 mm tables. The autoclave was purged with hydrogen and the reaction was started by heating the autoclave. The reaction mixture was stirred for 18 h at 205° C., the total pressure was maintained at 270 bar by purging hydrogen during the entire reductive amination step. After cooling down the autoclave the final product was collected, filtered, vented of excess ammonia and stripped in a rotary evaporator to remove light amines and water. A total of 560 grams of a low-color etheramine mixture was recovered. The analytical results thereof are shown in Table 1.

TABLE 1

| Total amine-value mg KOH/g | Total acetylatables mg KOH/g | Secondary and tertiary amine value mg KOH/g | Tertiary amine-value mg KOH/g | Hydroxyl value mg KOH/g | Degree of amination in % | Primary Amine in % of total amine |
|---|---|---|---|---|---|---|
| 277.66 | 282.50 | 4.54 | 0.86 | 5.70 | 98.59 | 98.36 |

Example 2

1 mol 2,2,4-Trimethyl-1,3-propane diol+4 mol propylene oxide, aminated a) 1 mol 2,2,4-Trimethyl-1,3-propane diol+4 mol propylene oxide 327.3 g molten 2,2,4-Trimethyl-1,3-pentane diol and 8.5 g KOH (50% in water) were dewatered for 2 h at 80° C. and <10 mbar in a 2 l autoclave. The autoclave was purged with nitrogen and heated to 140° C. 519.4 g propylene oxide was added in portions within 6 h. To complete the reaction, the mixture was allowed to post-react for additional 5 h at 140° C. The reaction mixture was stripped with nitrogen and volatile compounds were removed in vacuo at 80° C. The catalyst was removed by adding 2.5 g Macrosorb MP5plus, stirring at 100° C. for 2 h and filtration. A yellowish oil was obtained (825.0 g, hydroxy value: 172.3 mgKOH/g).

b) 1 mol 2,2,4-Trimethyl-1,3-propane diol+4 mol propylene oxide, aminated

In a 9 l autoclave 700 g of the resulting diol mixture from example 2-a, 1000 mL THF and 1500 g Ammonia were mixed in presence of 200 ml of a solid catalyst as described in EP0696572B1. The catalyst containing nickel, cobalt, copper, molybdenum and zirconium was in the form of 3×3 mm tables. The autoclave was purged with hydrogen and the reaction was started by heating the autoclave. The reaction mixture was stirred for 15 h at 205° C., the total pressure was maintained at 280 bar by purging hydrogen during the entire reductive amination step. After cooling down the autoclave the final product was collected, filtered, vented of excess ammonia and stripped in a rotary evaporator to remove light amines and water. A total of 670 grams of a low-color etheramine mixture was recovered. The analytical results thereof are shown in Table 2.

TABLE 2

| Total amine-value mg KOH/g | Total acetylatables mg KOH/g | Secondary and tertiary amine value mg KOH/g | Tertiary amine-value mg KOH/g | Hydroxyl value mg KOH/g | Degree of amination in % | Primary Amine in % of total amine |
|---|---|---|---|---|---|---|
| 179.70 | 224.80 | 0.45 | 0.21 | 45.31 | 79.86 | 99.75 |

Example 3

1 mol 2,2-Diethyl-1,3-propane diol+4 mol propylene oxide, aminated a) 1 mol 2,2-Diethyl-1,3-propane diol+4 mol propylene oxide 197.4 g molten 2,2-diethyl-1,3-propane diol and 5.4 g KOH (50% in water) were dewatered for 2 h at 80° C. and <10 mbar in a 2 l autoclave. The autoclave was purged with nitrogen and heated to 140° C. 346.4 g propylene oxide was added in portions within 4 h. To complete the reaction, the mixture was allowed to post-react for additional 5 h at 140° C. The reaction mixture was stripped with nitrogen and volatile compounds were removed in vacuo at 80° C. The catalyst was removed by adding 1.6 g Macrosorb MP5plus, stirring at 100° C. for 2 h and filtration. A yellowish oil was obtained (530.0 g, hydroxy value: 267.8 mgKOH/g).

b) 1 mol 2,2-Diethyl-1,3-propane diol+4 mol propylene oxide, aminated

In a 9 l autoclave 500 g of the resulting diol mixture from example 3-a, 1200 ml THF and 1500 g Ammonia were mixed in presence of 200 ml of a solid catalyst as described in EP0696572B1. The catalyst containing nickel, cobalt, copper, molybdenum and zirconium was in the form of 3×3 mm tables. The autoclave was purged with hydrogen and the reaction was started by heating the autoclave. The reaction mixture was stirred for 15 h at 205° C., the total pressure was maintained at 270 bar by purging hydrogen during the entire reductive amination step. After cooling down the autoclave the final product was collected, filtered, vented of excess ammonia and stripped in a rotary evaporator to remove light amines and water. A total of 470 grams of a low-color etheramine mixture was recovered. The analytical results thereof are shown in Table 3.

TABLE 3

| Total amine-value mg KOH/g | Total acetylatables mg KOH/g | Secondary and tertiary amine value mg KOH/g | Tertiary amine-value mg KOH/g | Hydroxyl value mg KOH/g | Degree of amination in % | Primary Amine in % of total amine |
|---|---|---|---|---|---|---|
| 292.40 | 300.88 | 3.78 | 0.72 | 9.20 | 96.95 | 98.71 |

Example 4

1 mol 2-Methyl-2-propyl-1,3-propandiol+4 mol propylene oxide, aminated a) 1 mol 2-Methyl-2-propyl-1,3-propandiol+4 mol propylene oxide 198.3 g molten 2-methyl-2-propyl-1,3-propanediol and 5.5 g KOH (50% in water) were dewatered for 2 h at 80° C. and <10 mbar in a 2 l autoclave. The autoclave was purged with nitrogen and heated to 140° C. 348.0 g propylene oxide was added in portions within 4 h. To complete the reaction, the mixture was allowed to post-react for additional 5 h at 140° C. The reaction mixture was stripped with nitrogen and volatile compounds were removed in vacuo at 80° C. The catalyst was removed by adding 1.6 g Macrosorb MP5plus, stirring at 100° C. for 2 h and filtration.

A yellowish oil was obtained (520.0 g, hydroxy value: 308.1 mgKOH/g).

b) 1 mol 2-Methyl-2-propyl-1,3-propandiol+4 mol propylene oxide, aminated

In a 9 l autoclave 500 g of the resulting diol mixture from example 4-a, 1200 ml THF and 1500 g ammonia were mixed in presence of 200 ml of a solid catalyst as described in EP0696572B1. The catalyst containing nickel, cobalt, copper, molybdenum and zirconium was in the form of 3×3 mm tables. The autoclave was purged with hydrogen and the reaction was started by heating the autoclave. The reaction mixture was stirred for 15 h at 205° C., the total pressure was maintained at 270 bar by purging hydrogen during the entire reductive amination step. After cooling down the autoclave the final product was collected, filtered, vented of excess ammonia and stripped in a rotary evaporator to remove light amines and water. A total of 470 grams of a low-color etheramine mixture was recovered. The analytical results thereof are shown in Table 4.

Example 5

1 mol 2-Ethyl-1,3-hexane diol+4 mol propylene oxide, aminated a) 1 mol 2-Ethyl-1,3-hexane diol+4 mol propylene oxide A 2 l autoclave was charged with 290.6 g molten 2-Ethyl-1,3-hexane diol and 7.5 g KOH (50% in water). The mixture was dewatered for 2 h at 90° C. and <10 mbar. The autoclave was purged with nitrogen and heated to 140° C. 461.1 g propylene oxide was added in portions within 4 h. To complete the reaction, the mixture was stirred for additional 5 h at 140° C. The reaction mixture was stripped with nitrogen and volatile compounds were removed in vacuo at 80° C. The catalyst was removed by adding 2.3 g Macrosorb MP5plus, stirring at 100° C. for 2 h and filtration.

A yellowish oil was obtained (745.0 g, hydroxy value: 229.4 mgKOH/g).

b) 1 mol 2-Ethyl-1,3-hexane diol+4 mol propylene oxide, aminated

In a 9 l autoclave 750 g of the resulting diol mixture from example 5-a, 950 ml THF and 1500 g Ammonia were mixed in presence of 200 ml of a solid catalyst as described in EP0696572B1. The catalyst containing nickel, cobalt, copper, molybdenum and zirconium was in the form of 3×3 mm tables. The autoclave was purged with hydrogen and the reaction was started by heating the autoclave. The reaction mixture was stirred for 15 h at 205° C., the total pressure was maintained at 270 bar by purging hydrogen during the entire reductive amination step. After cooling down the autoclave the final product was collected, filtered, vented of excess ammonia and stripped in a rotary evaporator to remove light amines and water. A total of 710 grams of a low-color etheramine mixture was recovered. The analytical results thereof are shown in Table 5.

TABLE 4

| Total amine-value mg KOH/g | Total acetylatables mg KOH/g | Secondary and tertiary amine value mg KOH/g | Tertiary amine-value mg KOH/g | Hydroxyl value mg KOH/g | Degree of amination in % | Primary Amine in % of total amine |
|---|---|---|---|---|---|---|
| 292.45 | 301.76 | 3.01 | 1.33 | 10.64 | 96.49 | 98.97 |

TABLE 5

| Total amine-value mg KOH/g | Total acetylatables mg KOH/g | Secondary and tertiary amine value mg KOH/g | Tertiary amine-value mg KOH/g | Hydroxyl value mg KOH/g | Degree of amination in % | Primary Amine in % of total amine |
|---|---|---|---|---|---|---|
| 288.21 | 301.10 | 3.32 | 0.50 | 13.39 | 95.56 | 98.85 |

Example 6

1 mol 2-Phenyl-2-methyl-1,3-propane diol+4 mol propylene oxide, aminated a) 1 mol 2-Phenyl-2-methyl-1,3-propane diol+4 mol propylene oxide

A 2 l autoclave was charged with 298.4 g 2-Phenyl-2-methyl-1,3-propane diol and 7.1 g KOH (50% in water) and heated to 120° C. The mixture was dewatered for 2 h at 120° C. and <10 mbar. The autoclave was purged with nitrogen and heated to 140° C. 408.6 g propylene oxide was added in portions within 4 h. To complete the reaction, the mixture was stirred for additional 5 h at 140° C. The reaction mixture was stripped with nitrogen and volatile compounds were removed in vacuo at 80° C. The catalyst was removed by adding 2.1 g Macrosorb MP5plus, stirring at 100° C. for 2 h and filtration.

A yellowish oil was obtained (690.0 g, hydroxy value: 266.1 mgKOH/g).

b) 1 mol 2-Phenyl-2-methyl-1,3-propane diol+4 mol propylene oxide, aminated

In a 9 l autoclave 600 g of the resulting diol mixture from example 6-a, 1100 ml THF and 1500 g Ammonia were mixed in presence of 200 ml of a solid catalyst as described in EP0696572B1. The catalyst containing nickel, cobalt, copper, molybdenum and zirconium was in the form of 3×3 mm tables. The autoclave was purged with hydrogen and the reaction was started by heating the autoclave. The reaction mixture was stirred for 15 h at 205° C., the total pressure was maintained at 270 bar by purging hydrogen during the entire reductive amination step. After cooling down the autoclave the final product was collected, filtered, vented of excess ammonia and stripped in a rotary evaporator to remove light amines and water. A total of 570 grams of a low-color etheramine mixture was recovered. The analytical results thereof are shown in Table 6.

TABLE 6

| Total amine-value mg KOH/g | Total acetylatables mg KOH/g | Secondary and tertiary amine value mg KOH/g | Tertiary amine-value mg KOH/g | Hydroxyl value mg KOH/g | Degree of amination in % | Primary Amine in % of total amine |
|---|---|---|---|---|---|---|
| 281.80 | 287.50 | 2.91 | 0.47 | 6.17 | 97.86 | 98.97 |

Example 7

1 mol 2,2-Dimethyl-1,3-propane diol+4 mol propylene oxide, aminated a) 1 mol 2,2-Dimethyl-1,3-propane diol+4 mol propylene oxide

A 2 l autoclave was charged with 208.3 g 2,2-Dimethyl-1,3-propane diol and 1.34 g potassium tert.-butylate and heated to 120° C. The autoclave was purged with nitrogen and heated to 140° C. 464 g propylene oxide was added in portions within 6 h. To complete the reaction, the mixture was stirred for additional 5 h at 140° C. The reaction mixture was stripped with nitrogen and volatile compounds were removed in vacuo at 80° C. The catalyst was removed by adding 1.1 g Macrosorb MP5plus, stirring at 100° C. for 2 h and filtration.

A light yellowish oil was obtained (650.0 g, hydroxy value: 308.6 mgKOH/g).

b) 1 mol 2,2-Dimethyl-1,3-propane diol+4 mol propylene oxide, aminated

In a 9 l autoclave 500 g of the resulting diol mixture from example 6-a, 1200 ml THF and 1500 g Ammonia were mixed in presence of 200 ml of a solid catalyst as described in EP0696572B1. The catalyst containing nickel, cobalt, copper, molybdenum and zirconium was in the form of 3×3 mm tables. The autoclave was purged with hydrogen and the reaction was started by heating the autoclave. The reaction mixture was stirred for 15 h at 205° C., the total pressure was maintained at 280 bar by purging hydrogen during the entire reductive amination step. After cooling down the autoclave the final product was collected, filtered, vented of excess ammonia and stripped in a rotary evaporator to remove light amines and water. A total of 450 grams of a low-color etheramine mixture was recovered. The analytical results thereof are shown in Table 7.

TABLE 7

| Total amine-value mg KOH/g | Total acetylatables mg KOH/g | Secondary and tertiary amine value mg KOH/g | Tertiary amine-value mg KOH/g | Hydroxyl value mg KOH/g | Degree of amination in % | Primary Amine in % of total amine |
|---|---|---|---|---|---|---|
| 329.86 | 338.00 | 1.66 | 0.90 | 9.04 | 97.33 | 99.50 |

Example 8

1 mol 2-butyl-2-ethyl-1,3-propanediol+5.6 mol propylene oxide, aminated a) 1 mol 2-butyl-2-ethyl-1,3-propanediol+5.6 mol propylene oxide In a 2 l autoclave 313.1 g 2-Butyl-2-ethyl-1,3-propanediol and 3.8 g KOH (50% in water) were mixed and stirred under vacuum (<10 mbar) at 120° C. for 2 h. The autoclave was purged with nitrogen and heated to 140° C. 635.6 g propylene oxide was added in portions within 6 h. To complete the reaction, the mixture was allowed to post-react for additional 5 h at 140° C. The reaction mixture was stripped with nitrogen and volatile compounds were removed in vacuo at 80° C. The catalyst was removed by adding 50.9 g water and 8.2 g phosphoric acid (40% in water) stirring at 100° C. for 0.5 h and dewatering in vacuo for 2 hours. After filtration 930.0 g of light yellowish oil was obtained (hydroxy value: 190 mgKOH/g).

b) 1 mol 2-butyl-2-ethyl-1,3-propanediol+5.6 mol propylene oxide, aminated

The amination of 8a (1 mol 2-butyl-2-ethyl-1,3-propanediol+5.6 mole propylene oxide) was conducted in a tubular reactor (length 500 mm, diameter 18 mm) which had been charged with 15 mL of silica (3×3 mm pellets) followed by 70 mL (74 g) of the catalyst precursor (containing oxides of nickel, cobalt, copper and tin on gamma-$Al_2O_3$, 1.0-1.6 mm split—prepared according to WO 2013/072289 A1) and filled up with silica (ca. 15 mL).

The catalyst was activated at atmospheric pressure by being heated to 100° C. with 25 Nl/h of nitrogen, then 3 hours at 150° C. in which the hydrogen feed was increased from 2 to 25 Nl/h, then heated to 280° C. at a heating rate of 60° C. per hour and kept at 280° C. for 12 hours. The reactor was cooled to 100° C., the nitrogen flow was turned off and the pressure was increased to 120 bar. The catalyst was flushed with ammonia at 100° C., before the temperature was increased to 206° C. and the alcohol feed was started with a WHSV of 0.19 kg/liter*h (molar ratio ammonia/alcohol=55:1, hydrogen/alcohol=11.6:1). The crude material was collected and stripped on a rotary evaporator to remove excess ammonia, light weight amines and reaction water to afford 8 b (1 mol 2-butyl-2-ethyl-1,3-propanediol+ 5.6 mole propylene oxide, aminated). The analytical data of the reaction product is shown in Table 8.

Use as Additives in Laundry Detergents

Technical stain swatches of blue knitted cotton containing Beef Fat, Pork Fat, Sausage Fat, Chicken Fat, Bacon Graese and Napolina Olive Oil were purchased from Warwick Equest Ltd. and washed in conventional western European washing machines (Miele Waschmaschine Softronic W 2241), selecting a 59 min washing cycle without heating and using 75 g of liquid detergent composition LA1 (table 9) together with or without 1.25 g of polyetheramine additive and some hydrochloric acid to readjust the pH after addition of the polyetheramine. The pH of 75 g of LA1 (Tab. 9) in 1 L water should be at pH=8.3. Water hardness was 2.5 mM ($Ca^{2+}$: $Mg^{2+}$ was 3:1). Standard colorimetric measurement was used to obtain L*, a* and b* values for each stain before and after the washing. From L*, a* and b* values the stain level was calculated.

Stain removal from the swatches was calculated as follows:

$$\text{Stain Removal Index } (SRI) = \frac{\Delta E_{initial} - \Delta E_{washed}}{\Delta E_{initial}} \times 100$$

$\Delta E_{initial}$=Stain level before washing
$\Delta E_{washed}$=Stain level after washing Four replicates for each stain type have been carried out. Given below are the averaged values. Stain level corresponds to the amount of grease on the fabric. The stain level of the fabric before the washing ($\Delta E_{initial}$) is high, in the washing process stains are removed and the stain level after washing is smaller ($\Delta E_{washed}$). The better the stains have been removed the lower the value for $\Delta E_{washed}$ will be and the higher the difference will be to $\Delta E_{initial}$. Therefore the value of stain removal index increases with better washing performance.

TABLE 9

| liquid detergent composition LA1 | |
|---|---|
| Ingredients of liquid detergent composition LA1 | percentage by weight |
| Alkyl Benzene sulfonate[1] | 7.50% |
| AE3S [2] | 2.60% |
| AE9 [3] | 0.40% |
| NI 45-7 [4] | 4.40% |
| Citric Acid | 3.20% |
| C1218 Fatty acid | 3.10% |
| Amphiphilic polymer[5] | 0.50% |

TABLE 8

| Total amine-value mg KOH/g | Total acetylatables mg KOH/g | Secondary and tertiary amine value mg KOH/g | Tertiary amine-value mg KOH/g | Hydroxyl value mg KOH/g | Grade of amination in % | Primary Amine in % of total amine |
|---|---|---|---|---|---|---|
| 222.92 | 231.50 | 2.57 | 0.31 | 8.89 | 96.16 | 98.85 |

TABLE 9-continued liquid detergent composition LA1

| Ingredients of liquid detergent composition LA1 | percentage by weight |
|---|---|
| Zwitterionic dispersant[6] | 1.00% |
| Ethoxylated Polyethyleneimine [7] | 1.51% |
| Protease[8] | 0.89% |
| Enymes[9] | 0.21% |
| Chelant[10] | 0.28% |
| Brightener[11] | 0.09% |
| Solvent | 7.35% |
| Sodium Hydroxide | 3.70% |
| Fragrance & Dyes | 1.54% |
| Water, filler, stucturant | To Balance |

[1] Linear alkylbenenesulfonate having an average aliphatic carbon chain length C11-C12 supplied by Stepan, Northfield Illinois, USA

[2] AE3S is C12-15 alkyl ethoxy (3) sulfate supplied by Stepan, Northfield, Illinois, USA

[3] AE9 is C12-14 alcohol ethoxylate, with an average degree of ethoxylation of 9, supplied by Huntsman, Salt Lake City, Utah, USA

[4] NI 45-7 is C14-15 alcohol ethoxylate, with an average degree of ethoxylation of 7, supplied by Huntsman, Salt Lake City, Utah, USA

[5] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

[6] A compound having the following general structure: bis(($C_2H_5O$)($C_2H_4O$)$n$)($CH_3$)—N+—$C_xH_{2x}$—N+—($CH_3$)-bis(($C_2H_5O$)($C_2H_4O$)$n$), wherein n = from 20 to 30, and x = from 3 to 8, or sulphated or sulphonated variants thereof

[7] Polyethyleneimine (MW = 600) with 20 ethoxylate groups per —NH

[8] Proteases may be supplied by Genencor International, Palo Alto, California, USA (e.g. Purafect Prime ®) or by Novozymes, Bagsvaerd, Denmark (e.g. Liquanase ®, Coronase ®).

[9] Natalase ®, Mannaway ® are all products of Novozymes, Bagsvaerd, Denmark.

[10] Suitable chelants are, for example, diethylenetetraamine pentaacetic acid (DTPA) supplied by Dow Chemical, Midland, Michigan, USA or Hydroxyethane di phosphonate (HEDP) or diethylene triamine penta(methyl phosphonic) acid supplied by Solutia, St Louis, Missouri, USA;

[11] Fluorescent Brightener 1 is Tinopal ® AMS, Fluorescent Brightener 2 supplied by Ciba Specialty Chemicals, Basel, Switzerland Washing Test 1: Initial Water Temperature at 24° C.

| Stain | A | B | C | D | E |
|---|---|---|---|---|---|
| Beef Fat | 69.1 | 66.4 | 76.3 | 76.2 | 77.4 |
| Pork Fat | 68.2 | 68.4 | 77.1 | 77.2 | 78.4 |
| Napolina Olive Oil | 47.0 | 47.0 | 59.8 | 55.7 | 57.4 |

A: liquid detergent composition LA1 (table 8) without additional polyetheramine additive
B: liquid detergent composition LA1 (table 8) with polyetheramine (2-Aminomethyl-ethyl)-omega-(2-aminomethylethoxy)-poly(oxy(methyl-1,2-ethandiyl)), sold under the trade name Polyetheramine ® D 230 or JEFFAMINE ® D-230.
C: liquid detergent composition LA1 (table 8) with polyetheramine of Example 1
D: liquid detergent composition LA1 (table 8) with polyetheramine of Example 4
E: liquid detergent composition LA1 (table 8) with polyetheramine of Example 6

Washing Test 2: Initial Water Temperature at 25° C.

| Stain | A | B | C |
|---|---|---|---|
| Sausage Fat | 64.6 | 66.6 | 73.6 |
| Chicken Fat | 63.0 | 65.9 | 74.4 |
| Bacon Grease | 67.1 | 72.0 | 75.5 |

A: liquid detergent composition LA1 (table 8) without additional polyetheramine additive
B: liquid detergent composition LA1 (table 8) with Polyetheramine ® D230
C: liquid detergent composition LA1 (table 8) with polyetheramine of Example 5

The superior grease cleaning effect obtained with the addition of the claimed 1,3 propandiol-based polyetheramine compounds is clearly shown.

Washing Test 3: Initial Water Temperature at 24.5° C.

| Stain | A | B |
|---|---|---|
| Pork Fat | 65.3 | 68.7 |
| Chicken Fat | 59.3 | 68.3 |
| Bacon Graese | 64.9 | 74.1 |

A: liquid detergent composition LA1 (table 8) without additional polyetheramine additive
B: liquid detergent composition LA1 (table 8) with polyetheramine of example 7

Washing Test 4: Initial water temperature at 18° C.

Technical stain swatches of blue knitted cotton containing Beef Fat, Pork Fat and Chicken Fat were purchased from Warwick Equest Ltd. and washed in conventional western European washing machines (Miele Waschmaschine Softronic W 2241), selecting a 59 min washing cycle without heating (wash at 18° C.) and using 75 g of liquid detergent composition LA1 (see Table 9) together with or without 0.75 g of etheramine additive and some hydrochloric acid to readjust the pH. The pH of 75 g of LA1 (Tab. 9) in 1 L water should be at pH=8.3.

| Stain | A | B | C |
|---|---|---|---|
| Beef Fat | 73.5 | 77.4 | 73.5 |
| Pork Fat | 73.3 | 76.6 | 72.7 |
| Chicken Fat | 75.6 | 78.4 | 75.4 |

A: liquid detergent composition LA1 (see Table 9) without additional etheramine additive
B: liquid detergent composition LA1 (see Table 9) with polyetheramine of example 8.
C: liquid detergent composition LA1 (see Table 9) with polyetheramine (2-Aminomethylethyl)-omega-(2-aminomethylethoxy)-poly(oxy(methyl-1,2-ethandiyl)), sold under the trade name Polyetheramine ® D 230 or JEFFAMINE ® D-230

The cleaning composition with the etheramine according to the invention (see Washing Test 4B) shows superior grease cleaning effects over the detergent composition without etheramines (see Washing Test 4A) and also shows superior grease cleaning effects over the cleaning composition with the etheramine of the comparative example (Washing Test 4C).

Application Tests

In the following examples, the individual ingredients within the cleaning compositions are expressed as percentages by weight of the cleaning compositions.

Example I: Comparative Grease Stain Removal from NA Laundry Detergent Compositions The following laundry detergent compositions are prepared by traditional means known to those of ordinary skill in the art by mixing the listed ingredients. Composition A is a conventional premium laundry detergent that uses Baxxodur® EC301 comprising a linear amine-terminated polyalkylene glycol with the structure of Formula A.

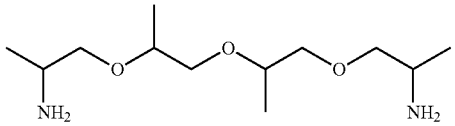

Formula A

Detergent compositions B and C each contain an etheramine mixture comprising 2-Butyl-2-ethyl-1,3-propanediol+2.0 propylene oxide/OH, aminated, preparation of polyetheramine described in Example 1 (Formula B).

Formula B

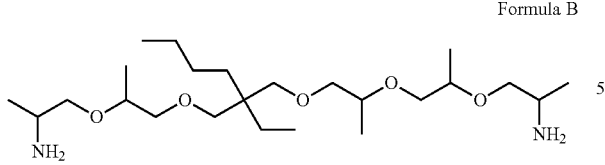

Stain removal index scores for each stain were calculated and are listed in the table below:

| | Liquid Detergent A (wt %) | Liquid Detergent B (wt %) | Liquid Detergent C (wt %) |
|---|---|---|---|
| AES $C_{12-15}$ alkyl ethoxy (1.8) sulfate | 10.9 | 10.9 | 10.9 |
| Alkyl benzene sulfonate [2] | 1.56 | 1.56 | 1.56 |
| Sodium formate | 2.66 | 2.66 | 2.66 |
| Sodium hydroxide | 0.21 | 0.21 | 0.21 |
| Monoethanolamine (MEA) | 1.65 | 1.65 | 1.65 |
| Diethylene glycol (DEG) | 4.10 | 4.10 | 4.10 |
| AE9[3] | 0.40 | 0.40 | 0.40 |
| C16AE7 | 3.15 | 3.15 | 3.15 |
| Baxxodur EC301 | 1.04 | — | — |
| Polyetheramine[11] | — | 1.04 | 2.30 |
| Chelant[4] | 0.18 | 0.18 | 0.18 |
| Citric Acid | 1.70 | 1.70 | 1.70 |
| $C_{12-18}$ Fatty Acid | 1.47 | 1.47 | 1.47 |
| Borax | 1.19 | 1.19 | 1.19 |
| Ethanol | 1.44 | 1.44 | 1.44 |
| Ethoxylated Polyethyleneimine [1] | 1.35 | 1.35 | 1.35 |
| A compound having the following general structure: bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n = from 20 to 30, and x = from 3 to 8, or sulphated or sulphonated variants thereof | 0.40 | 0.40 | 0.40 |
| 1,2-Propanediol | 2.40 | 2.40 | 2.40 |
| Protease (54.5 mg active/g)[9] | 0.89 | 0.89 | 0.89 |
| Mannanase: Mannaway ® (25.6 mg active/g)[5] | 0.04 | 0.04 | 0.04 |
| Amylase: Natalase ® (29 mg active/g)[5] | 0.14 | 0.14 | 0.14 |
| Fluorescent Whitening Agents[10] | 0.10 | 0.10 | 0.10 |
| Water, perfume, dyes & other components | | Balance | |

[1] Polyethyleneimine (MW = 600) with 20 ethoxylate groups per —NH.
[2] Linear alkylbenzenesulfonate having an average aliphatic carbon chain length $C_{11}$-$C_{12}$ supplied by Stepan, Northfield, Illinois, USA
[3] AE9 is $C_{12-13}$ alcohol ethoxylate, with an average degree of ethoxylation of 9, supplied by Huntsman, Salt Lake City, Utah, USA
[4] Suitable chelants are, for example, diethylenetetraamine pentaacetic acid (DTPA) supplied by Dow Chemical, Midland, Michigan, USA or Hydroxyethane di phosphonate (HEDP) supplied by Solutia, St Louis, Missouri, USA Bagsvaerd, Denmark
[5] Natalase ®, Mannaway ® are all products of Novozymes, Bagsvaerd, Denmark.
6. Proteases may be supplied by Genencor International, Palo Alto, California, USA (e.g. Purafect Prime ®) or by Novozymes, Bagsvaerd, Denmark (e.g. Liquanase ®, Coronase ®).
[10] Suitable Fluorescent Whitening Agents are for example, Tinopal ® AMS, Tinopal ® CBS-X, Sulphonated zinc phthalocyanine Ciba Specialty Chemicals, Basel, Switzerland
[11] 2-Butyl-2-ethyl-1,3-propane diol + 2.0 propylene oxide/OH, aminated, preparation of polyetheramine described in Example 1.

Technical stain swatches of CW120 cotton containing US clay, Frank's® Hot Sauce, hamburger grease, Italian dressing, and make up were purchased from Empirical Manufacturing Co., Inc (Cincinnati). The swatches were washed in a Whirlpool® front loader washing machine, using 6 grains per gallon water hardness and washed at 100 degrees Fahrenheit. The total amount of liquid detergent used in the test was 49 grams.

Image analysis was used to compare each stain to an unstained fabric control. Software converted images taken into standard colorimetric values and compared these to standards based on the commonly used Macbeth Colour Rendition Chart, assigning each stain a colorimetric value (Stain Level). Eight replicates of each were prepared.

Stain removal from the swatches was measured as follows:

$$\text{Stain Removal Index } (SRI) = \frac{\Delta E_{initial} - E_{washed}}{\Delta E_{initial}} \times 100$$

$\Delta E_{initial}$ = Stain level before washing $\Delta E_{washed}$ = Stain level after washing

| Stain | Composition A SRI | Composition B SRI | Composition C SRI | LSD |
|---|---|---|---|---|
| US Clay | 54.4 | 58.7 | 57.7 | 4.0 |
| Frank's Hot Sauce | 31.0 | 34.1 | 35.3 | 3.2 |
| Hamburger Grease | 60.0 | 64.6 | 67.4 | 3.9 |
| Italian Dressing | 77.4 | 79.4 | 82.7 | 2.6 |
| Make-up | 37.4 | 38.4 | 41.3 | 2.3 |

These results illustrate the surprising grease removal benefit of an etheramine compound comprising compounds of Formula I and/or II (as used in Compositions B and C), as compared to a linear polyalkylene glycol with terminal primary amines (Composition A).

Example II: Comparative Grease Removal from Laundry Cleaning Powder Composition

The following laundry detergent compositions are prepared by traditional means known to those of ordinary skill in the art by mixing the listed ingredients. Composition A is a conventional premium laundry detergent that contains no amine-terminated polyalkylene glycol compound. Composition B is a laundry detergent that uses Baxxodur®EC301, a linear amine-terminated polyalkylene glycol (see Formula A above).

Composition C is a detergent that uses a polyetheramine comprising 2-Butyl-2-ethyl-1,3-propane diol+2.0 propylene oxide/OH, aminated, preparation of polyetheramine described in Example 1 (Formula B above).

compositions. Image analysis was used to compare each stain to an unstained fabric control. Software converted images taken into standard colorimetric values and compared these to standards based on the commonly used Macbeth Colour Rendition Chart, assigning each stain a colorimetric value (Stain Level). Eight replicates of each were prepared. The stain removal index was then calculated according to the formula shown above.

|  | Powder Detergent A (wt %) | Powder Detergent B (wt %) | Powder Detergent C (wt %) |
|---|---|---|---|
| Linear alkylbenzenesulfonate[1] | 8.2 | 8.2 | 8.2 |
| AE3S[2] | 1.9 | 1.9 | 1.9 |
| Zeolite A[3] | 1.8 | 1.8 | 1.8 |
| Citric Acid | 1.5 | 1.5 | 1.5 |
| Sodium Carbonate[5] | 29.7 | 29.7 | 29.7 |
| Silicate 1.6R ($SiO_2$:$Na_2O$)[4] | 3.4 | 3.4 | 3.4 |
| Soil release agent[6] | 0.2 | 0.2 | 0.2 |
| Acrylic Acid/Maleic Acid Copolymer[7] | 2.2 | 2.2 | 2.2 |
| Carboxymethylcellulose | 0.9 | 0.9 | 0.9 |
| Protease—Purafect ® (84 mg active/g)[9] | 0.08 | 0.08 | 0.08 |
| Amylase—Stainzyme Plus ® (20 mg active/g)[8] | 0.16 | 0.16 | 0.16 |
| Lipase—Lipex ® (18.00 mg active/g)[8] | 0.24 | 0.24 | 0.24 |
| Cellulase—Celluclean ™ (15.6 mg active/g)[8] | 0.1 | 0.1 | 0.1 |
| Baxxodur EC301 | — | 1.0 | — |
| Polyetheramine[10] | — | — | 1.0 |
| TAED [11] | 3.26 | 3.26 | 3.26 |
| Percarbonate[12] | 14.1 | 14.1 | 14.1 |
| Na salt of Ethylenediamine-N,N'-disuccinic acid, (S,S) isomer (EDDS)[13] | 2.19 | 2.19 | 2.19 |
| Hydroxyethane di phosphonate (HEDP)[14] | 0.54 | 0.54 | 0.54 |
| $MgSO_4$ | 0.38 | 0.38 | 0.38 |
| Perfume | 0.38 | 0.38 | 0.38 |
| Suds suppressor agglomerate[15] | 0.04 | 0.04 | 0.04 |
| Sulphonated zinc phthalocyanine (active)[16] | 0.0012 | 0.0012 | 0.0012 |
| Sulfate/Water & Miscellaneous | Balance | Balance | Balance |

[1]Linear alkylbenzenesulfonate having an average aliphatic carbon chain length $C_{11}$-$C_{12}$ supplied by Stepan, Northfield, Illinois, USA
[2]AE3S is $C_{12-15}$ alkyl ethoxy (3) sulfate supplied by Stepan, Northfield, Illinois, USA
[3]Zeolite A is supplied by Industrial Zeolite (UK) Ltd, Grays, Essex, UK
[4]1.6R Silicate is supplied by Koma, Nestemica, Czech Republic
[5]Sodium Carbonate is supplied by Solvay, Houston, Texas, USA
[6]Soil release agent is Repel-o-tex ® PF, supplied by Rhodia, Paris, France
[7]Acrylic Acid/Maleic Acid Copolymer is molecular weight 70,000 and acrylate:maleate ratio 70:30, supplied by BASF, Ludwigshafen, Germany
[8]Savinase ®, Natalase ®, Stainzyme ®, Lipex ®, Celluclean ™, Mannaway ® and Whitezyme ® are all products of Novozymes, Bagsvaerd, Denmark.
[9]Proteases may be supplied by Genencor International, Palo Alto, California, USA (e.g. Purafect Prime ®) or by Novozymes, Bagsvaerd, Denmark (e.g. Liquanase ®, Coronase ®).
[10]2-Butyl-2-ethyl-1,3-propane diol + 2.0 propylene oxide/OH, aminated, preparation of polyetheramine described in Example 1
[11] TAED is tetraacetylethylenediamine, supplied under the Peractive ® brand name by Clariant GmbH, Sulzbach, Germany
[12]Sodium percarbonate supplied by Solvay, Houston, Texas, USA
[13]Na salt of Ethylenediamine-N,N'-disuccinic acid, (S,S) isomer (EDDS) is supplied by Octel, Ellesmere Port, UK
[14]Hydroxyethane di phosphonate (HEDP) is supplied by Dow Chemical, Midland, Michigan, USA
[15]Suds suppressor agglomerate is supplied by Dow Corning, Midland, Michigan, USA
[16]Fluorescent Brightener 1 is Tinopal ® AMS, Fluorescent Brightener 2 is Tinopal ® CBS-X, Sulphonated zinc phthalocyanine and Direct Violet 9 is Pergasol ® Violet BN-Z all supplied by Ciba Specialty Chemicals, Basel, Switzerland Technical stain swatches of cotton CW120 containing bacon grease, burnt butter, dirty motor oil, hamburger grease, Italian dressing, lipstick, margarine, pizza sauce, taco grease were purchased from Empirical Manufacturing Co., Inc (Cincinnati). The stained swatches were washed in conventional western European washing machines (Meile®) using 14 grains per gallon hardness, selecting the cotton cycle at 30° C., using 80 g of each of the respective detergent Key results are summarized in the following table:

| Stain | Composition A SRI | Composition B SRI | Composition C SRI | LSD |
|---|---|---|---|---|
| Bacon Grease | 88.8 | 88.6 | 90.6 | 1.0 |
| Burnt Butter | 95.6 | 96.1 | 96.8 | 0.6 |

| Stain | Composition A SRI | Composition B SRI | Composition C SRI | LSD |
|---|---|---|---|---|
| Dirty Motor Oil | 31.3 | 32.6 | 35.8 | 2.8 |
| Hamburger Grease | 73.6 | 82.5 | 85.8 | 5.8 |
| Italian Dressing | 90.2 | 91.1 | 92.5 | 1.2 |
| Lipstick | 72.4 | 70.7 | 75.2 | 12.6 |
| Margarine | 82.8 | 88.0 | 94.1 | 3.2 |
| Pizza Sauce | 70.2 | 72.6 | 74.9 | 11.1 |
| Taco Grease | 69.8 | 77.8 | 94.0 | 8.0 |

These results illustrate the surprising grease removal benefit of the polyetheramine compound comprising compounds of Formula I and/or II (as used in Composition C), as compared to a linear polyalkylene glycol with terminal primary amines (Composition B) and a conventional (nil-polyetheramine) powdered detergent, especially on difficult-to-remove, high-frequency consumer stains like hamburger grease and taco grease.

Example III: Comparative Grease Removal from WE Laundry Liquid Compositions

The following laundry detergent compositions are prepared by traditional means known to those of ordinary skill in the art by mixing the listed ingredients. Composition A is a conventional premium laundry detergent that contains no amine-terminated polyalkylene glycol compound. Composition B is a detergent that uses a polyetheramine comprising two terminal primary amines and two alkyl branches (specifically, 2-Butyl-2-ethyl-1,3-propane diol+2.0 propylene oxide/OH, aminated, preparation of polyetheramine described in Example 1 Formula B above).

| | WE Liquid HDL A (wt %) | WE Liquid HDL B (wt %) |
|---|---|---|
| AE3S[4] | 2.6 | 2.6 |
| Alkyl benzene sulfonate [3] | 7.5 | 7.5 |
| Sodium formate/Calcium formate | 0.4 | 0.4 |
| Sodium hydroxide | 3.7 | 3.7 |
| Monoethanolamine (MEA) | 0.3 | 0.3 |
| Diethylene glycol (DEG) | 0.8 | 0.8 |
| AE9[6] | 0.4 | 0.4 |
| AE7[5] | 4.4 | 4.4 |
| Polyetheramine[11] | — | 1.0 |
| Chelant[7] | 0.3 | 0.3 |
| Citric Acid | 3.2 | 3.2 |
| $C_{12-18}$ Fatty Acid | 3.1 | 3.1 |
| Ethanol | 2.0 | 2.0 |
| Ethoxylated Polyethylenimine [1] | 1.5 | 1.5 |
| Amphiphilic polymer [2] | 0.5 | 0.5 |
| A compound having the following general structure: bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n = from 20 to 30, and x = from 3 to 8, or sulphated or sulphonated variants thereof | 1.0 | 1.0 |
| 1,2-Propanediol | 3.9 | 3.9 |
| Protease (40.6 mg active/g)[9] | 0.6 | 0.6 |
| Amylase: Stainzyme ® (15 mg active/g)[8] | 0.2 | 0.2 |
| Fluorescent Whitening Agents[10] | 0.1 | 0.1 |
| Water, perfume, dyes & other components | Balance | |

[1] Polyethyleneimine (MW = 600) with 20 ethoxylate groups per —NH.
[2] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[3] Linear alkylbenzenesulfonate having an average aliphatic carbon chain length $C_{11}$-$C_{12}$ supplied by Stepan, Northfield, Illinois, USA
[4] AE3S is $C_{12-15}$ alkyl ethoxy (3) sulfate supplied by Stepan, Northfield, Illinois, USA
[5] AE7 is $C_{12-15}$ alcohol ethoxylate, with an average degree of ethoxylation of 7, supplied by Huntsman, Salt Lake City, Utah, USA
[6] AE9 is $C_{12-13}$ alcohol ethoxylate, with an average degree of ethoxylation of 9, supplied by Huntsman, Salt Lake City, Utah, USA
[7] Suitable chelants are, for example, diethylenetetraamine pentaacetic acid (DTPA) supplied by Dow Chemical, Midland, Michigan, USA or Hydroxyethane di phosphonate (HEDP) supplied by Solutia, St Louis, Missouri, USA Bagsvaerd, Denmark
[8] Savinase ®, Natalase ®, Stainzyme ®, Lipex ®, Celluclean ™, Mannaway ® and Whitezyme ® are all products of Novozymes, Bagsvaerd, Denmark.
[9] Proteases may be supplied by Genencor International, Palo Alto, California, USA (e.g. Purafect Prime ®) or by Novozymes, Bagsvaerd, Denmark (e.g. Liquanase ®, Coronase ®).
[10] Suitable Fluorescent Whitening Agents are for example, Tinopal ® AMS, Tinopal ® CBS-X, Sulphonated zinc phthalocyanine Ciba Specialty Chemicals, Basel, Switzerland
[11] 2-Butyl-2-ethyl-1,3-propane diol + 2.0 propylene oxide/OH, aminated, preparation of polyetheramine described in Example 1.

Technical stain swatches of cotton CW120 containing bacon grease, burnt butter, dirty motor oil, hamburger grease, Italian dressing, lipstick, margarine, pizza sauce, taco grease were purchased from Empirical Manufacturing Co., Inc (Cincinnati). The stained swatches were washed in conventional western European washing machines (Miele®) using 14 grains per gallon hardness, selecting the cotton cycle at 30° C., using 80 g of each of the respective detergent composition. Image analysis was used to compare each stain to an unstained fabric control. Software converted images taken into standard colorimetric values and compared these to standards based on the commonly used Macbeth Colour Rendition Chart, assigning each stain a colorimetric value (Stain Level). Eight replicates of each were prepared. The stain removal index was then calculated according to the formula shown above.

Key results are summarized in the following table:

| Stain | Composition A SRI | Composition B SRI | LSD |
|---|---|---|---|
| Bacon Grease | 84.6 | 90.8 | 2.8 |
| Burnt Butter | 84.9 | 95.5 | 2.3 |
| Dirty Motor Oil | 53.9 | 71.4 | 21.7 |
| Hamburger Grease | 61.0 | 82.7 | 5.3 |
| Italian Dressing | 90.1 | 92.3 | 1.8 |
| Makeup | 52.6 | 55.7 | 2.2 |
| Margarine | 74.4 | 90.6 | 3.7 |
| Taco Grease | 61.7 | 79.2 | 3.1 |

These results illustrate the surprising grease removal benefit of an etheramine mixture comprising compounds of Formula I and/or II (as used in Composition B), as compared to a conventional (nil-polyetheramine) liquid detergent, especially on difficult-to-remove, high-frequency consumer stains like hamburger grease and taco grease.

Example IV: Comparative Grease Removal in a Powder Additive

The following laundry detergent compositions are prepared by traditional means known to those of ordinary skill in the art by mixing the listed ingredients. Composition A is a powder additive that contains no amine-terminated polyalkylene glycol compound. Composition B is a powder additive that uses a polyetheramine comprising 2-Butyl-2-ethyl-1,3-propane diol+2.0 propylene oxide/OH, aminated, preparation of polyetheramine described in Example 1 Formula B above).

Technical stain swatches were purchased from Warwick Equest Ltd. and washed in conventional western European washing machines (Ariston Hotpoint), selecting the cotton cycle at 30° C., using 80 g of a marketed commercial liquid detergent composition (i.e., Ariel Liquid Actilift) and 30 g of powder additive, Composition A, which contains no amine-terminated polyalkylene glycol compound, or Composition B, a powder additive that uses a polyetheramine comprising 2-Butyl-2-ethyl-1,3-propane diol+2.0 propylene oxide/OH, aminated, preparation of polyetheramine described in Example 1, Formula B above).

Image analysis was used to compare each stain to an unstained fabric control. Software converted images taken into standard colorimetric values and compared these to standards based on the commonly used Macbeth Colour Rendition Chart, assigning each stain a colorimetric value (Stain Level). Eight replicates of each were prepared. The stain removal index was then calculated according to the formula above.

Statistical significance on a 95% confidence level was calculated using standard statistical methods (Student's t-test) and is shown with an "s" nest to the stain removal index.

Key results are summarized in the following tables:

| Ingredients | Powder Additive A (wt %) | Powder Additive B (wt %) | Powder Additive C (wt %) |
| --- | --- | --- | --- |
| Sodium percarbonate[5] | 33.0 | 33.0 | 33.0 |
| Tetraacetyl ethylene diamine[4] | 10.0 | 10.0 | 10.0 |
| nonanoyloxybenzene sulphonate[7] | 7.5 | 7.5 | 7.5 |
| Polyetheramine[3] | — | — | 4.0 |
| Baxxodur EC301 | — | 4.0 | — |
| C12-C16 Alkylbenzene sulphonic acid | 1.2 | 1.2 | 1.2 |
| C14-C15 alkyl 7-ethoxylate[6] | 0.25 | 0.25 | 0.25 |
| Mannanase [1] | 0.2 | 0.2 | 0.2 |
| Cellulase [2] | 0.2 | 0.2 | 0.2 |
| Brightener[8] | 0.1 | 0.1 | 0.1 |
| Sodium sulphate | Balance | Balance | Balance |

[1] Mannaway, from Novozymes (Denmark), 4 mg active enzyme per gram.
[2] Celluclean, from Novozymes (Denmark), 15.6 mg active enzyme per gram.
[3] 2-Butyl-2-ethyl-1,3-propane diol + 2,0 propylene oxide/OH, aminated, preparation of polyetheramine described in Example 1
[4] TAED is tetraacetylethylenediamine, supplied under the Peractive ® brand name by Clariant GmbH, Sulzbach, Germany
[5] Sodium percarbonate supplied by Solvay, Houston, Texas, USA
[6] AE7 is $C_{14-15}$ alcohol ethoxylate, with an average degree of ethoxylation of 7, supplied by Huntsman, Salt Lake City, Utah, USA
[7] NOBS is sodium nonanoyloxybenzenesulfonate, supplied by Future Fuels, Batesville, Arkansas, USA
[8] Suitable Fluorescent Whitening Agents are for example, Tinopal ® AMS, Tinopal ® CBS-X, Sulphonated zinc phthalocyanine Ciba Specialty Chemicals, Basel, Switzerland

| Stain | Liquid Detergent + Powder Additive A SRI | Liquid Detergent + Powder Additive B SRI |
| --- | --- | --- |
| Bacon Grease | 39.4 | 40.5 |
| Lard | 41.1 | 42.3 |
| Beef fat | 50.0 | 52.8 |
| Burnt Butter | 46.1 | 47.0 |
| Hamburger Grease | 49.7 | 51.9 |

| Stain | Liquid Detergent + Powder Additive A SRI | Liquid Detergent + Powder Additive C SRI |
| --- | --- | --- |
| Bacon Grease | 47.9 | 63.5s |
| Lard | 44.3 | 58.8s |
| Pork fat | 47.1 | 61.6s |
| Burnt Butter | 68.8 | 76.4s |
| Chicken Fat | 46.0 | 59.5s |

These results illustrate the surprising grease removal benefit of an etheramine mixture comprising compounds of Formula I and/or II (as used in Composition B) compared to conventional WE liquid detergent that does not contain branched amine-terminated polyakylene glycols, in 30 C Miele wash cycle.

Application of the Amines as Hardener in Epoxy Systems

Example 1

Preparation of the Reaction Resin Molding Material and Investigation of Reactivity Profile The compared formulations were prepared by mixing of stoichiometric amounts of amine with a liquid epoxy resin based on bisphenol-A-diglycidyl ether (EEW 182).

The rheological measurements for investigating the reactivity profile of the amines with epoxy resins were carried out at a shear stress controlled plate-plate rheometer (MCR 301, Anton Paar) with a plate diameter of 15 mm and a gap distance of 0.25 mm at different temperatures.

Analysis 1: Comparison of the time to reach a viscosity of 10000 mPa*s at a defined temperature: The measurement was carried out using the before mentioned rheometer at different temperatures (10° C., 23° C., 75° C.) (rotating). Comparison of gel time: The measurement was carried out using the before mentioned rheometer at different temperatures (10° C., 23° C., 40° C., 75° C.) (rotating-oscillating). The gel time is given by the inspection of loss modulus (G") and storage modulus (G').

| | a Viscosity increase to 10.000 mPas | | | | b Gel time | |
| --- | --- | --- | --- | --- | --- | --- |
| | 23° C. | | 75° C. | | 23° C. | 75° C. |
| Name | Initial viscosity Ø 2-5 min [mPas] | time [min] | Initial viscosity Ø 2-5 min [mPas] | time [min] | time [min] | time [min] |
| A | 886 | 478 | 39 | 40 | 1850 | 60 |
| B | 71 | 737 | 34 | 59 | 1534 | 90.5 |
| C | 304 | 1269 | 60 | 39 | 2090 | 52 |
| D | 836 | 721 | 36 | 68 | 2966 | 104 |
| E | 822 | 762 | 27 | 68 | 3050 | 99 |
| F | 535 | 471 | 26 | 56 | 2114 | 124 |
| G | 787 | 709 | 31 | 58 | 2633 | 85 |

A: polyetheramine (2-Aminomethylethyl)-omega-(2-aminomethylethoxy)-poly(oxy(methyl-1,2-ethandiyl)), sold under the trade name Polyetheramine® D 230 or JEFFAMINE® D-230

B: Polyetheramine with the following structure, sold under the tradename XTJ568®:

$H_2N$—[structure with O repeating n times]—$NH_2$ n = 2,5

C: Poly[oxy(methyl-1,2-ethanediyl)], α-hydro-ω-(2-aminomethylethoxy)-, ether with 2-ethyl-2-(hydroxymethyl)-1,3-propanediol (3:1), CAS-Nr.: 39429-51-3, sold under the trade name Polyetheramine T 403 or JEFFAMINE T-403

D: 2-Butyl-2-ethyl-1,3-propane diol+2.0 propylene oxide/OH, aminated, synthesis described in example 1

E: 2-Butyl-2-ethyl-1,3-propane diol+2.0 propylene oxide/OH, aminated, synthesis described in example 1, second batch F: 1 mol 2-butyl-2-ethyl-1,3-propanediol+1.0 mole propylene oxide, aminated, synthesis described in comparative example 1

G: 2,2-Dimethyl-1,3-propane diol+2 PO/OH, aminated, synthesis described in comparative example 7

Example 2

Exothermic Profile of Reaction Resin Molding Material and Glass Temperatures of the Cured Thermosets The DSC-measurements of the curing reaction of the amines with a liquid epoxy resin based on bisphenol-A-diglycidyl ether (EEW 182) for determination of onset temperature ($T_O$), exotherm ($\Delta E$) as well as glass temperature ($T_g$) was carried out according to ASTM D 3418.

Analysis 2a) Temperature program for the DSC-measurements: 0° C.→5K/min 180° C.→30 min 180° C.→20K/min 0° C.→20K/min 220° C.

| 2 Name | DSC a Onset [° C.] | ΔH [J/g] | Tg [° C.] |
| --- | --- | --- | --- |
| A | 83.3 | 421.9 | 93 |
| B | 91.6 | 425.9 | 91.8 |
| C | 84.3 | 399.3 | 90.3 |
| D | 88.2 | 263.2 | 67.8 |
| E | 90.1 | 349 | 67.8 |
| F | 80.3 | 300.2 | 67.8 |
| G | 88.1 | 372.3 | 73.9 |

A: polyetheramine (2-Aminomethylethyl)-omega-(2-aminomethylethoxy)-poly(oxy(methyl-1,2-ethandiyl)), sold under the trade name Polyetheramine® D 230 or JEFFAMINE® D-230

B: Polyetheramine with the following structure, sold under the tradename XTJ568®:

$H_2N$—[structure with O repeating n times]—$NH_2$ n = 2,5

C: Poly[oxy(methyl-1,2-ethanediyl)], α-hydro-ω-(2-aminomethylethoxy)-, ether with 2-ethyl-2-(hydroxymethyl)-1,3-propanediol (3:1), CAS-Nr.: 39429-51-3, sold under the trade name Polyetheramine® D 230 or JEFFAMINE® D-230.

D: 2-Butyl-2-ethyl-1,3-propane diol+2.0 propylene oxide/OH, aminated, synthesis described in example 1

E: 2-Butyl-2-ethyl-1,3-propane diol+2.0 propylene oxide/OH, aminated, synthesis described in example 1, second batch F: 1 mol 2-butyl-2-ethyl-1,3-propanediol+1.0 mole propylene oxide, aminated, synthesis described in comparative example 1

G: 2,2-Dimethyl-1,3-propane diol+2 PO/OH, aminated, synthesis described in comparative example 7

Results:

D; E and G show a longer open time at 23° C. compared to F, the time to reach 10.000 mPas is significantly longer. On the other hand, at 75° C., D and E show a faster overall curing which are measured by the gel time. This is an advantage for the workability of the epoxy systems because the reactive components are usually mixed at ambient temperature and cured at higher temperatures later.

D and E show similar Tgs compared to F. This means we have a better reactivity profile with similar thermomechanical properties.

The invention claimed is:

1. An etheramine mixture comprising at least 90% by weight, based on the total weight of the etheramine mixture, of an amine of Formula (I) and (II), Formula (I)

$$Z_1-A_1\!\!-\!\!\left[O\!-\!A_2\right]_{(y_1-1)}\!\!\left[O\!\!-\!\!A_3\right]_{(y-1)}\!\!\underset{R_1\ R_2\ R_3\ R_4\ R_5\ R_6}{\underset{O\quad\ O}{\diagup\!\!\diagdown}}\!\!A_4\!-\!O\!\left[\!A_5\!-\!O\right]_{(x-1)}\!\!\left[A_6\right]_{(x_1-1)}\!\!-\!Z_2$$

Formula (II)

$$R_7\ R_8\underset{R_9\ R_{10}}{Z_3}\!\!\underset{O}{\diagup\!\!\diagdown}\!\!\left[\!A_7\!-\!O\right]_{(x-1)+(y-1)+1}\!\!\left[A_8\!-\!O\right]_{(x_1-1)+(y_1-1)}\!\!A_9\!-\!Z_4\ R_{11}\ R_{12}$$

wherein $R_1$-$R_{12}$ are independently H, alkyl, cycloalkyl, aryl, alkylaryl, or arylalkyl, wherein at least one of $R_1$-$R_6$ and at least one of $R_7$-$R_{12}$ is not H,
  wherein $A_1$-$A_9$ are independently linear or branched alkylenes having 2 to 18 carbon atoms,
  wherein $Z_1$-$Z_4$ are independently OH, $NH_2$, NHR' or NR'R", wherein at least one of $Z_1$-$Z_2$ and at least one of $Z_3$-$Z_4$ is $NH_2$, NHR' or NR'R", wherein R' and R" are independently alkylenes having 2 to 6 carbon atoms,
  and wherein the sum of x+y is in the range of from 3 to 20,
  wherein x≥1 and y≥1; and $x_1+y_1$ is in the range of from 2 to 200, wherein $x_1$≥1 and $y_1$≥1.

2. The etheramine mixture according to claim 1, wherein the etheramine mixture comprises at least 95% by weight, based on the total weight of the etheramine mixture, of the amine of Formula (I) and (II).

3. The etheramine mixture according to claim 1, wherein in said polyetheramine of Formula (I) or Formula (II), the degree of amination is in the range of 60% to 100%.

4. The etheramine mixture according to claim 1, wherein in said polyetheramine of Formula (I) or Formula (II), $A_1$-$A_9$ are independently selected from the group consisting of ethylene, propylene, and butylene.

5. The etheramine mixture according to claim 1, wherein in said polyetheramine of Formula (I) or Formula (II), each of $A_1$-$A_9$ is propylene.

6. The etheramine mixture according to claim 1, wherein in said polyetheramine of Formula (I) or Formula (II), $R_1$, $R_2$, $R_5$, $R_6$, $R_7$, $R_8$, $R_{11}$, and $R_{12}$ are H and $R_3$, $R_4$, $R_9$, and $R_{10}$ are independently C1-16 alkyl or aryl.

7. The etheramine mixture according to claim 1, wherein in said polyetheramine of Formula (I) or Formula (II), $R_1$, $R_2$, $R_5$, $R_6$, $R_7$, $R_8$, $R_{11}$, and $R_{12}$ are H and $R_3$, $R_4$, $R_9$, and $R_{10}$ are independently a butyl group, an ethyl group, a methyl group, a propyl group, or a phenyl group.

8. The etheramine mixture according to claim 1, wherein in said polyetheramine Formula (I) or Formula (II), $R_3$ and $R_9$ are each an ethyl group, $R_1$, $R_2$, $R_5$ $R_6$, $R_7$, $R_8$, $R_{11}$, $R_{12}$ are each H, $R_4$ and $R_{10}$ are each a butyl group.

9. The etheramine mixture according to claim 1, wherein the polyetheramine of Formula (I) or Formula (II) has a weight average molecular weight of about 290 to about 1000 grams/mole.

10. A process for the manufacture of an etheramine mixture comprising at least 90% by weight, based on the total weight of the etheramine mixture, of an etheramine of Formula (I) and (II) comprising the following steps:
   a) reacting a 1,3-diol of Formula (III) with $C_2$-$C_{18}$ alkylene oxides, wherein the molar ratio of 1,3-diol to $C_2$-$C_{18}$ alkylene oxides is in the range of 1:3 to 1:8,

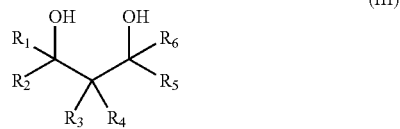

(III)

wherein $R_1$-$R_6$ are independently of one another H, alkyl, cycloalkyl, aryl, alkylaryl, or arylalkyl and at least one group selected from $R_1$-$R_6$ is not H, to form an alkoxylated 1,3-diol; and
   b) aminating the alkoxylated 1, 3-diol with ammonia.

11. The process for the manufacture of an etheramine mixture according to claim 10, further comprising reacting the polyetheramine of Formula (I) or Formula (II) obtained in step b) with an acid.

12. The process according to claim 10, wherein the molar ratio of 1,3-diol to $C_2$-$C_{18}$ alkylene oxides is in the range of 1:3 to 1:8.

13. The process according to claim 10, wherein the molar ratio of 1,3-diol to $C_2$-$C_{18}$ alkylene oxides is in the range of 1:4 to 1:6.

14. The process according to claim 10, wherein the $C_2$-$C_{18}$ alkylene oxides are selected from the group consisting of ethylene oxide, propylene oxide, butylene oxide and mixtures thereof.

15. The process according to claim 10, wherein the $C_2$-$C_{18}$ alkylene oxide is propylene oxide.

16. The process according to claim 10, wherein the 1,3-diol of formula (III) is selected from the group consisting of 2-butyl-2-ethyl-1,3-propanediol, 2-methyl-2-propyl-1,3-propanediol, 2-methyl-2-phenyl-1,3-propanediol, 2,2-dimethyl-1,3-propandiol, and 2-ethyl-1,3-hexandiol.

17. The process according to claim 10, wherein the amination is carried out in the presence of a copper-, nickel- or cobalt-containing catalyst.

18. The process according to claim 17, wherein the catalytically active material of the catalysts, before the reduction thereof with hydrogen, comprises oxygen compounds of aluminum, of copper, of nickel and of cobalt, and in the range from 0.2 to 5.0% by weight of oxygen compounds of tin, calculated as SnO.

19. A shampoo or body wash formulation comprising the etheramine mixture of claim 1.

20. A curing agent for epoxy resins or a reactant in the production of polymers comprising the etheramine mixture of claim 1.

21. The etheramine mixture of claim 1, wherein $A_1$-$A_9$ are independently linear or branched alkylenes having 2 to 10 carbon atoms.

22. The etheramine mixture of claim 1, wherein $A_1$-$A_9$ are independently linear or branched alkylenes having 2 to 5 carbon atoms.

23. The etheramine mixture of claim 1, wherein $x_1+y_1$ is in the range of from 2 to 20.

24. The etheramine mixture of claim 1, wherein $x_1+y_1$ is in the range of from 2 to 10.

* * * * *